United States Patent
Heng et al.

(10) Patent No.: US 11,802,057 B2
(45) Date of Patent: Oct. 31, 2023

(54) PLUMBED IN-LINE SENSOR SYSTEM FOR SWIMMING POOLS AND SPAS

(71) Applicant: ZODIAC POOL SYSTEMS LLC, Carlsbad, CA (US)

(72) Inventors: Hwa Heng, Carlsbad, CA (US); Ricky Lo, Carlsbad, CA (US); Anthony Levacque, Carlsbad, CA (US)

(73) Assignee: ZODIAC POOL SYSTEMS LLC, Carlsbad, CA (US)

( * ) Notice: Subject to any disclaimer, the term of this patent is extended or adjusted under 35 U.S.C. 154(b) by 0 days.

(21) Appl. No.: 17/476,781

(22) Filed: Sep. 16, 2021

(65) Prior Publication Data
US 2022/0089459 A1    Mar. 24, 2022

Related U.S. Application Data (60) Provisional application No. 63/081,121, filed on Sep. 21, 2020.

(51) Int. Cl.
| | | |
|---|---|---|
| C02F 1/00 | (2023.01) | |
| E04H 4/12 | (2006.01) | |
| C02F 103/42 | (2006.01) | |

(52) U.S. Cl.
CPC ........... *C02F 1/008* (2013.01); *E04H 4/1209* (2013.01); *C02F 2103/42* (2013.01); *C02F 2209/06* (2013.01)

(58) Field of Classification Search
CPC .. C02F 1/008; C02F 2103/42; C02F 2209/06; E04H 4/1209; G01N 1/2035; G01N 2001/1031; G01N 33/1893

USPC .......................................................... 210/85
See application file for complete search history.

(56) References Cited

U.S. PATENT DOCUMENTS

| | | | |
|---|---|---|---|
| 6,625,824 B1 * | 9/2003 | Lutz | E04H 4/12 137/625.21 |
| 8,887,556 B2 * | 11/2014 | Silveri | G01N 33/18 73/61.41 |
| 2015/0203376 A1 | 7/2015 | Heng et al. | |
| 2016/0204528 A1 * | 7/2016 | Moser | H01R 11/22 439/40 |
| 2020/0271635 A1 | 8/2020 | Key et al. | |

FOREIGN PATENT DOCUMENTS

CN    110171852    8/2019

OTHER PUBLICATIONS

International Application No. PCT/US2021/050633, International Search Report and Written Opinion dated Nov. 26, 2021, 13 pages.
International Application No. PCT/US2021/050633, International Preliminary Report on Patentability dated Mar. 30, 2023, 10 pages.

\* cited by examiner

*Primary Examiner* — Ekandra S. Miller-Cruz
(74) *Attorney, Agent, or Firm* — Kilpatrick Townsend & Stockton LLP (57) ABSTRACT

A sensor system for swimming pools and spas is detailed herein. The sensor system can include one or more sensors positioned in a sensor housing located within a cavity of a pipe and in-line with an inlet and an outlet of the pipe. The sensor housing can divert a portion of water flowing through the cavity to an interior of the sensor housing and to an area around the sensors and maintain at least some of the diverted water in the area around the sensors even if the water is not flowing through or is drained from the pipe.

26 Claims, 11 Drawing Sheets

PLUMBED IN-LINE SENSOR SYSTEM FOR SWIMMING POOLS AND SPAS

REFERENCE TO RELATED APPLICATION

This application claims the benefit of U.S. Provisional Application No. 63/081,121, filed on Sep. 21, 2020 and entitled Plumbed In-Line Sensor System for Swimming Pools and Spas, the entire contents of which are hereby incorporated by reference.

FIELD OF THE INVENTION

This invention relates to sensor systems in liquid-containing bodies such as, but not limited to, swimming pools and spas.

BACKGROUND

For pool systems, it may be desirable to measure an oxidation reduction potential (ORP) or pH of the water. ORP is a measure of the ability to oxidize contaminants in the water. The pH is a measure of the degree of acidity or basicity of water. For safety purposes, it may be desirable to maintain the ORP above a threshold and to maintain a pH in a predefined range. A sensor system in the pool can be used to measure the pH and/or ORP.

Conventional sensor systems include sensors mounted in the main plumbing line. These systems expose the sensors to the main flow of the line, and excessive flow may lead to shorter sensor life. Additionally, conventional systems may allow the sensors to dry out if the pipes are drained, potentially damaging the sensors. Other conventional systems include a sensor housing mounted off the pipe, which requires additional fittings and tubing. These systems also require additional space on the piping and additional installation effort for water bonds (e.g., electrical bonds to the pool water) to reduce stray current in the water.

SUMMARY

According to certain embodiments of the present disclosure, a sensor system for a swimming pool or spa includes a sensor, a sensor housing, and an electronic assembly. The sensor housing may be positioned within the pipe so that water flowing in a bidirectional manner between an inlet and an outlet of the pipe encounters the sensor housing. The sensor housing may be configured to limit a flow of the water within the pipe that is capable of reaching the sensor, even though at least a portion of the sensor may be positioned within the pipe between the inlet and the outlet. The sensor housing also may be configured to maintain at least some water around the sensor, even if water is drained from the pipe and/or water ceases to flow through the pipe.

According to certain embodiments of the present disclosure, a sensor system includes a sensor and a sensor housing mounted within a cavity of a pipe. The sensor housing is configured to limit an amount of water flowing through the cavity that reaches the sensor, slow a speed of the limited amount of water before it reaches the sensor, and/or maintain a presence of at least some of the limited amount of water in contact with the sensor, even if the pipe is drained or no water is flowing through the cavity.

According to certain embodiments of the present disclosure, a sensor system includes a sensor and a sensor housing within a cavity of a pipe. The sensor housing houses at least a portion of the sensor and controls how much water moving through the cavity of the pipe reaches the sensor. The sensor system is configured to determine, based on sensor data, if (i) the oxidative reduction potential of the water is below a predefined threshold or (ii) the pH of the water is outside a predefined range and output an indicator based on the determination.

Various implementations described herein can include additional systems, methods, features, and advantages, which cannot necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The specification makes reference to the following appended figures.

DETAILED DESCRIPTION

The subject matter of embodiments of the present disclosure is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described. Directional references such as "up," "down," "top," "bottom," "left," "right," "front," and "back," among others, are intended to refer to the orientation as illustrated and described in the figure (or figures) to which the components and directions are referencing.

Disclosed herein are devices, such as sensor systems, for monitoring properties of water in a swimming pool or spa or other body of water. The sensor systems are designed so they may be positioned "in-line" with a pipe of the swimming pool or spa, so that water flowing through the pipe encounters the sensor systems. Even though the sensor systems may be positioned in-line with the pipe, the sensor systems are designed to limit flow of water to sensors of the sensor systems, and are also designed to keep the sensors wet if the pipes are drained. Additionally, the sensor systems are designed for easy installation with few wires and tubes.

A sensor system can include one or more sensors, a sensor housing, and one or more sensor ports. Each of these components may be mounted directly on and/or housed within a cavity of a pipe that provides a bi-directional flow path for the water. The one or more sensors can measure properties of the water, such as, but not limited to, an oxidative reduction potential (ORP) and/or a pH of the water. The sensor housing may be positioned within the cavity of the pipe and, in some cases, within a bidirectional flow path of water moving through the pipe. The sensor housing may surround the sensors to prevent the entirety of the flow of water moving through the pipe from reaching the sensor. Said another way, the sensors may be positioned within an interior of the sensor housing that is shielded from the main flow of water moving through the pipe.

In some examples, the sensor housing may include a baffle for directing a portion of the main flow of water moving through the pipe to the interior of the sensor housing and to an area around the sensors. In this way, the sensor housing is configured so that only the directed portion of water is permitted to contact the sensors, while the remainder of the main flow of water flowing through the pipe (e.g., the non-directed portion) does not contact the sensors. The sensor housing may also include a well in which tips of the sensors are positioned, where the well is configured to collect at least some of the directed water in the interior of the sensor housing such that water remains surrounding the sensors even if the pipe is drained or water stops flowing through the pipe.

The sensor ports may be positioned on an external surface of an electronic assembly to connect the sensors to the electronic assembly for reading the sensors. The proximity of the sensors to the sensor ports can allow for short sensor cables (e.g., less wiring) for connecting the sensors to the electronic assembly. The electronic assembly can determine if sensor data from the sensors is within predefined thresholds and output an indication if the sensor data is outside any of the thresholds.

In some cases, the electronic assembly includes a system that includes a non-transitory computer-readable medium having instructions stored thereon. The instructions are executable by a processing device to read sensor data from the sensor about one or more properties of the water. Additionally, the instructions are executable to determine if the sensor data indicates the one or more properties are outside a predefined threshold. The instructions are executable to output an indication based on determining the one or more properties are outside the predefined threshold.

FIGS. 1A-1D illustrate an exemplary plumbed in-line sensor system 5. The plumbed in-line sensor system 5 includes a pipe 15 and a cover 10. The pipe 15 includes a cavity that provides a bi-directional flow path for water of a swimming pool or spa or other body of water between an inlet 12 and an outlet 14 of the pipe 15. The cover 10 may couple with a housing of the sensor system 5 and be positioned over the sensing components of the plumbed in-line sensor system 5. The sensing components may measure ORP, pH, and/or other properties of the water.

Figure 1A:
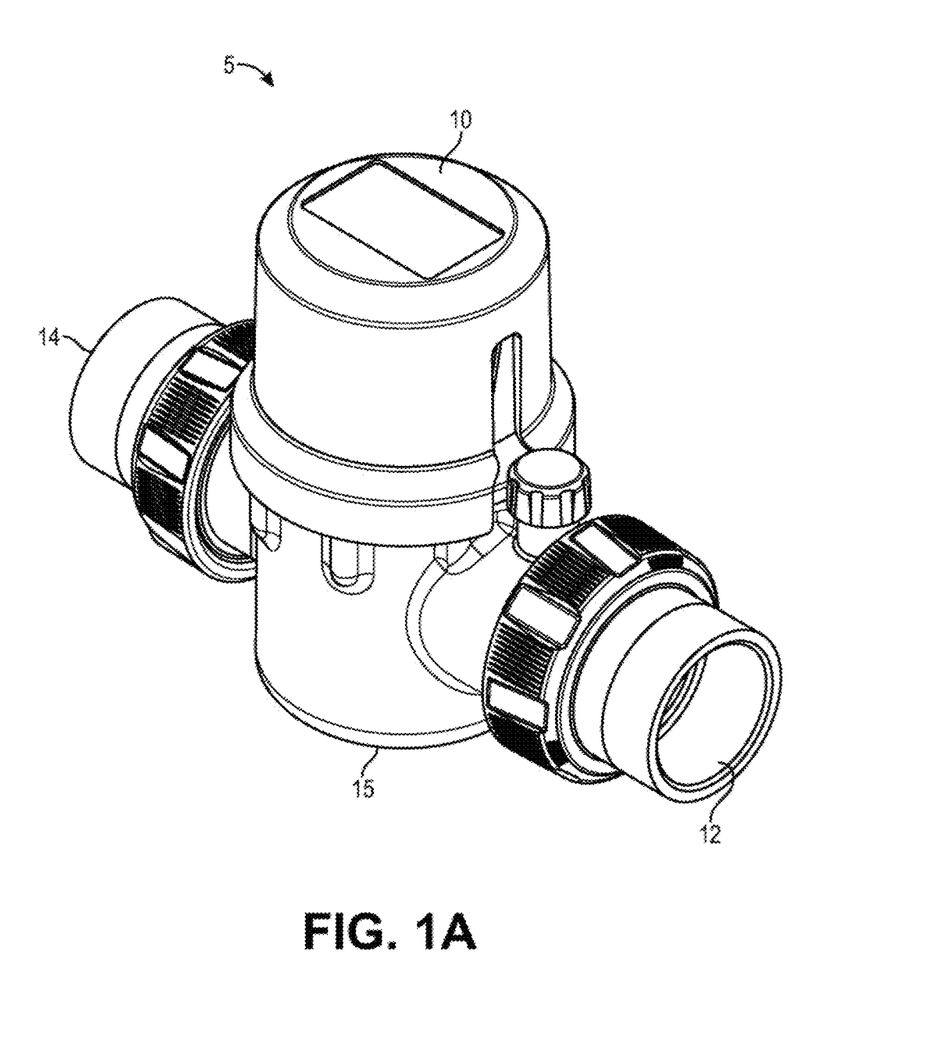
FIGS. 1A-1D are views of a plumbed in-line sensor system, according to embodiments.
Figure 1B:
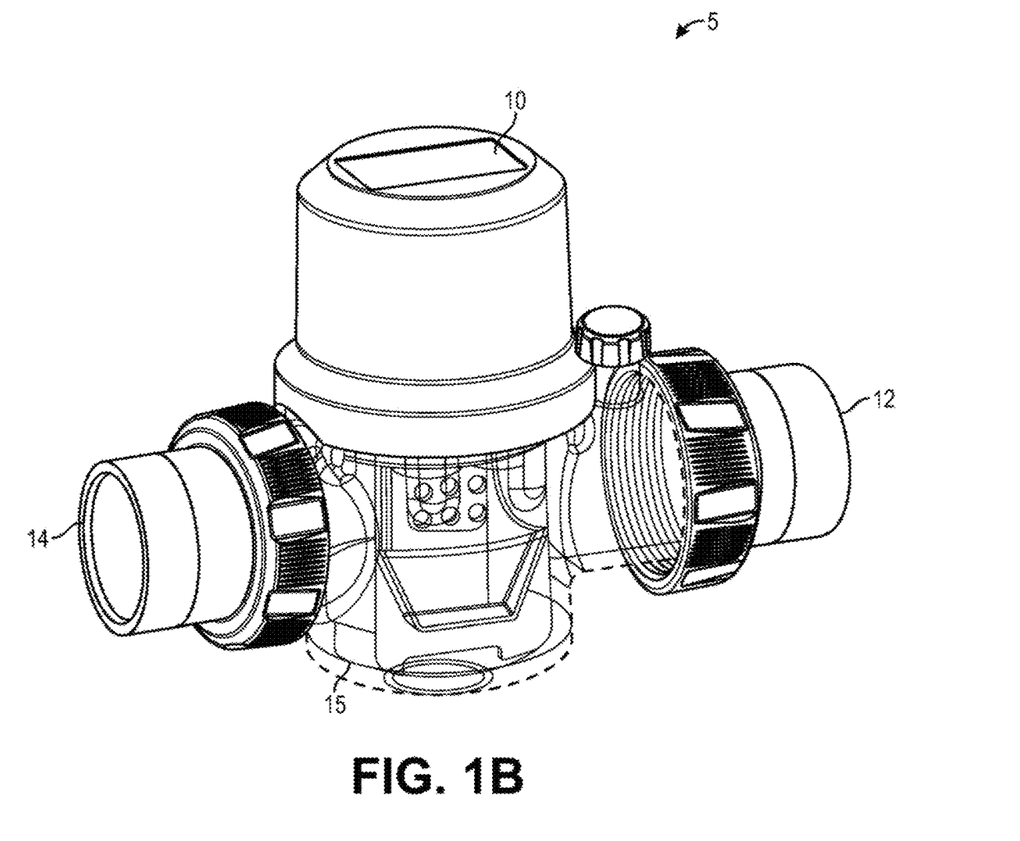
Figure 1C:
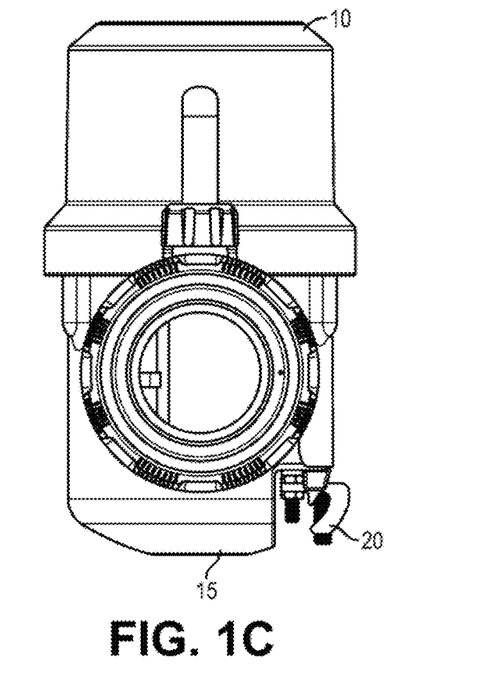
Figure 1D:
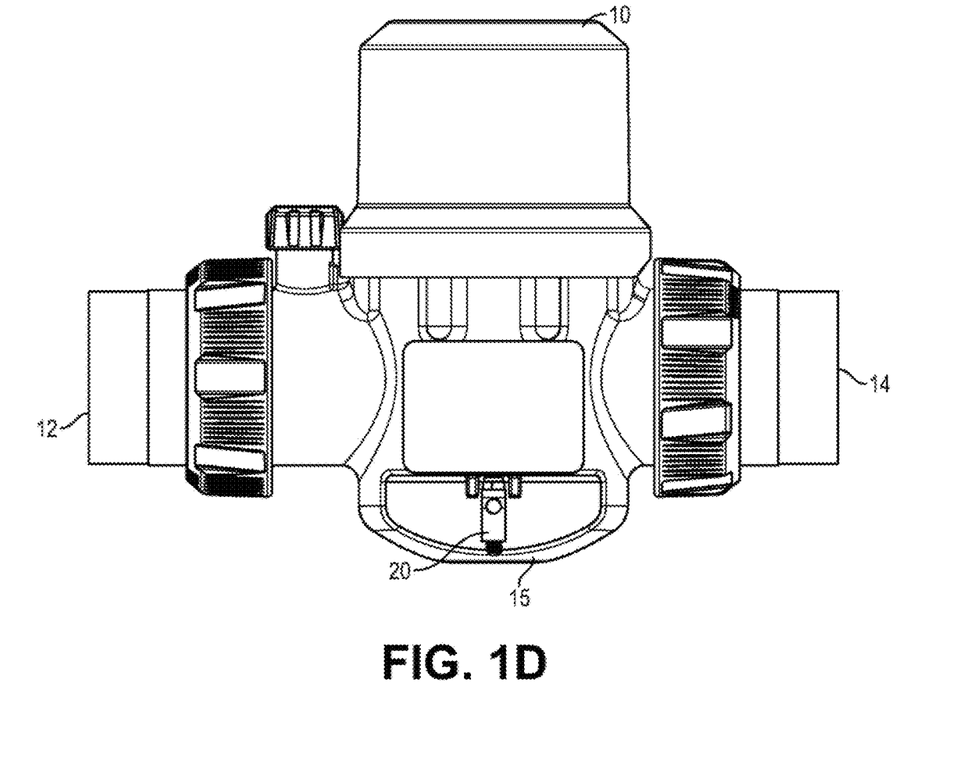

As shown in FIGS. 1C and 1D, the plumbed in-line sensor system 5 may include a water bond 20 coupled to the pipe 15. The water bond 20 may be an electrical bond to the pool water and can protect the sensing components from stray current. Additionally, the water bond 20 may also prevent stray current from entering the water. In some cases, the water bond 20 is installed separately from the sensor housing described below. In other cases, the water bond 20 is integrated with the sensor housing.

Figure 2A:
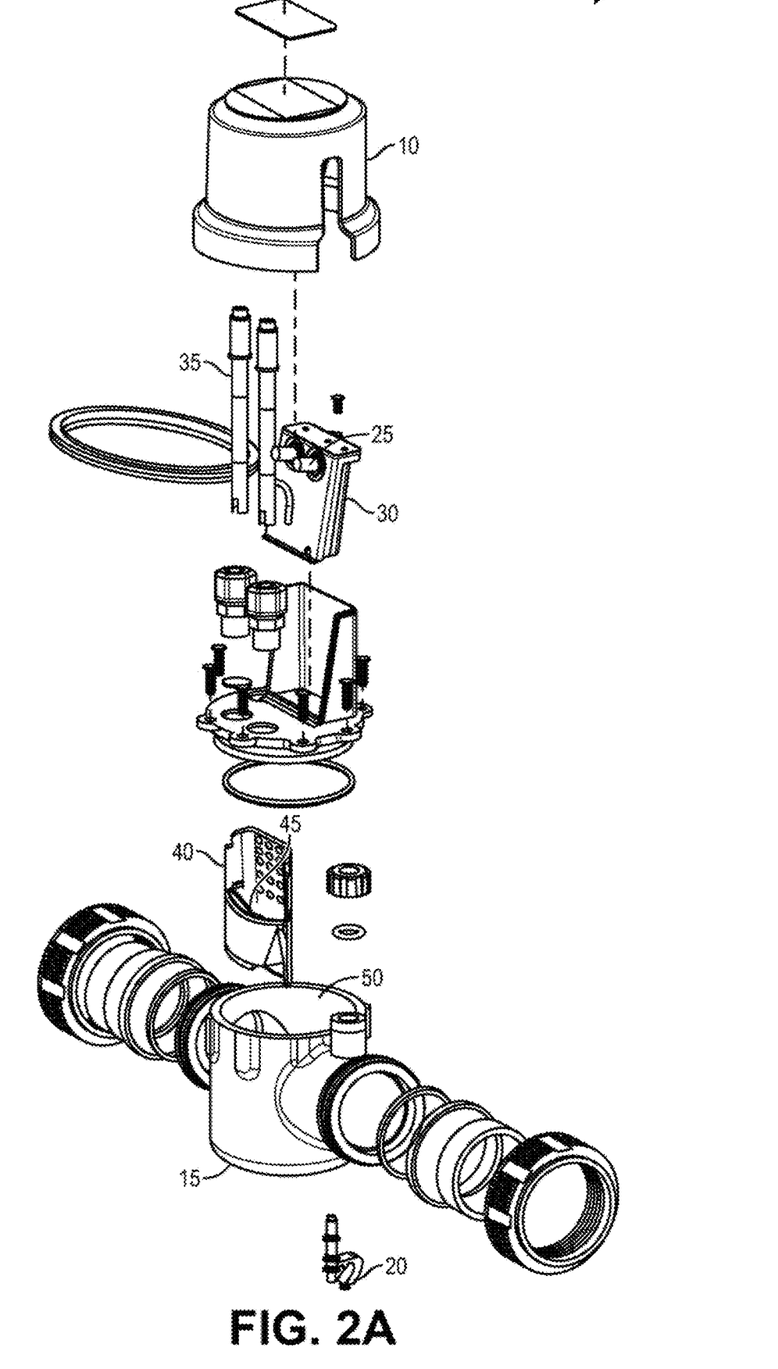
FIG. 2A is an exploded view of the plumbed in-line sensor system of FIG. 1.
Figure 2B:
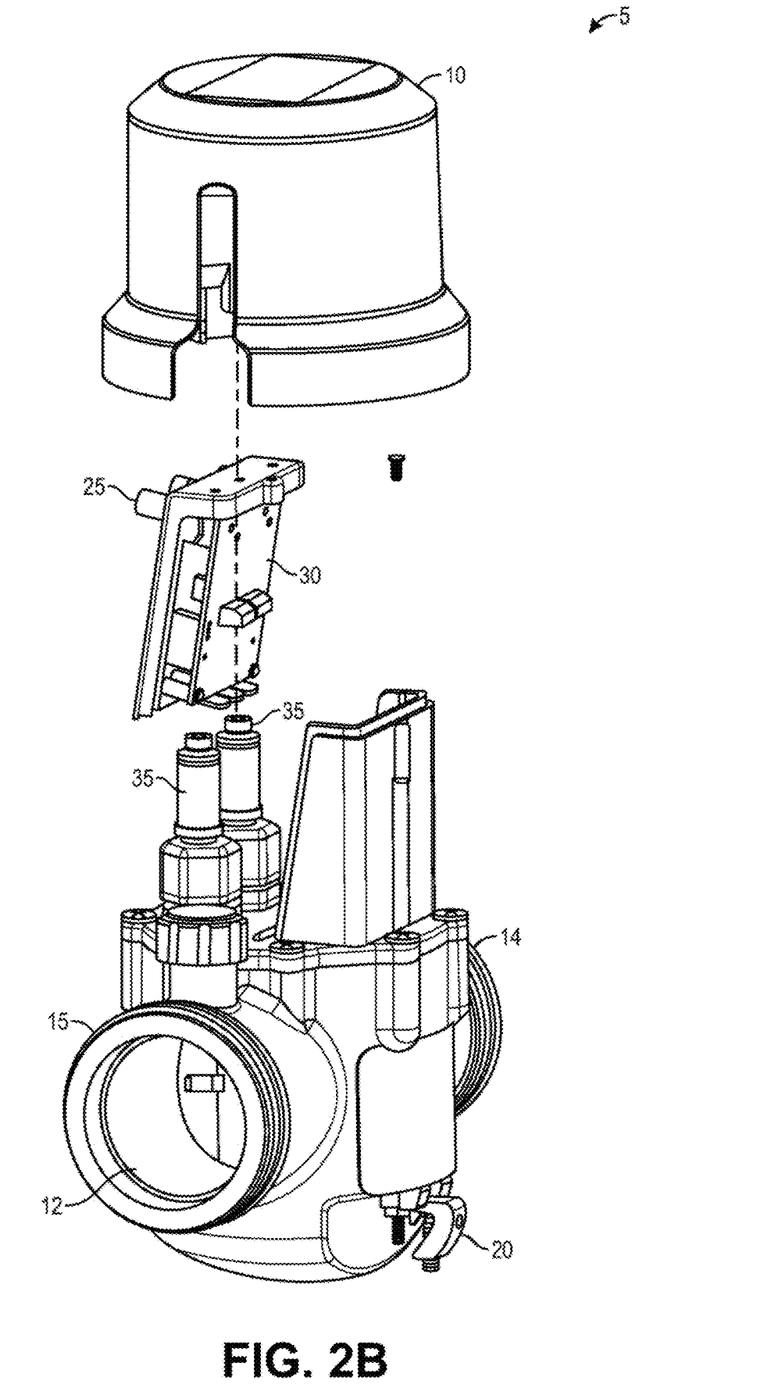
FIG. 2B is a partially-exploded view of the plumbed in-line sensor system of FIG. 1.

FIGS. 2A and 2B illustrate exemplary exploded views of a plumbed in-line sensor system 5. The sensor system includes the cover 10, the pipe 15, and the water bond 20 as previously described. The sensor system additionally includes one or more sensor ports 25, an electronic assembly 30, one or more sensors 35, and a sensor housing 40 with a well 45. The sensor housing 40 is located within a cavity 50 of the pipe 15 that extends between the inlet 12 and the outlet 14 and thus the sensor housing 40 is within the main path of water flowing between the inlet 12 and the outlet 14. In the illustrated example, the sensor system includes two sensor ports 25 and two sensors 35, although the sensor system may include only one sensor and one sensor port, or more than two sensors and more than two sensor ports, as desired.

In some cases, at least a portion of the one or more sensors 35 extends and/or is housed within the sensor housing 40. The one or more sensors 35 may extend into the pipe 15 to measure properties (e.g., the ORP and/or pH) of water flowing through the cavity 50 of the pipe 15 between the inlet 12 and the outlet 14. Each of the one or more sensors 35 may connect to one of the sensor ports 25 through sensor cables (not shown). The sensor ports 25 may connect to the electronic assembly 30, which may be mounted under the cover 10 for easy service and replacement. The electronic assembly 30 may include functionality that reads sensor data from the one or more sensors 35 regarding the measured properties. In some examples, the electronics assembly 30 is integrated with or otherwise in close proximity with the sensor housing 40, as the one or more of the sensors 35 (such as pH and/or ORP sensors) may produce an analog signal containing the sensor data and thus including the sensor electronics in close proximity to the sensors 35 may be beneficial due to the sensitivity of analog signals. The electronic assembly 30 may additionally include or connect to a computing device that outputs data from the one or more sensors 35. The output may also include an indication (e.g., light, alarm, etc.) based on data from the sensors 35 indicating the properties are outside a predefined threshold. For example, there may be a predefined threshold for the ORP, and the computing device outputs the indication if the data from the sensors 35 indicates the sensed ORP is below the threshold. Additionally, there may be a predefined range for the pH and the computing device may output the indication if the data from the sensors 35 indicates the sensed pH is outside of the range. In some examples, the electronic assembly 30 may communicate (digitally or otherwise) with a pool automation system.

Figure 3:
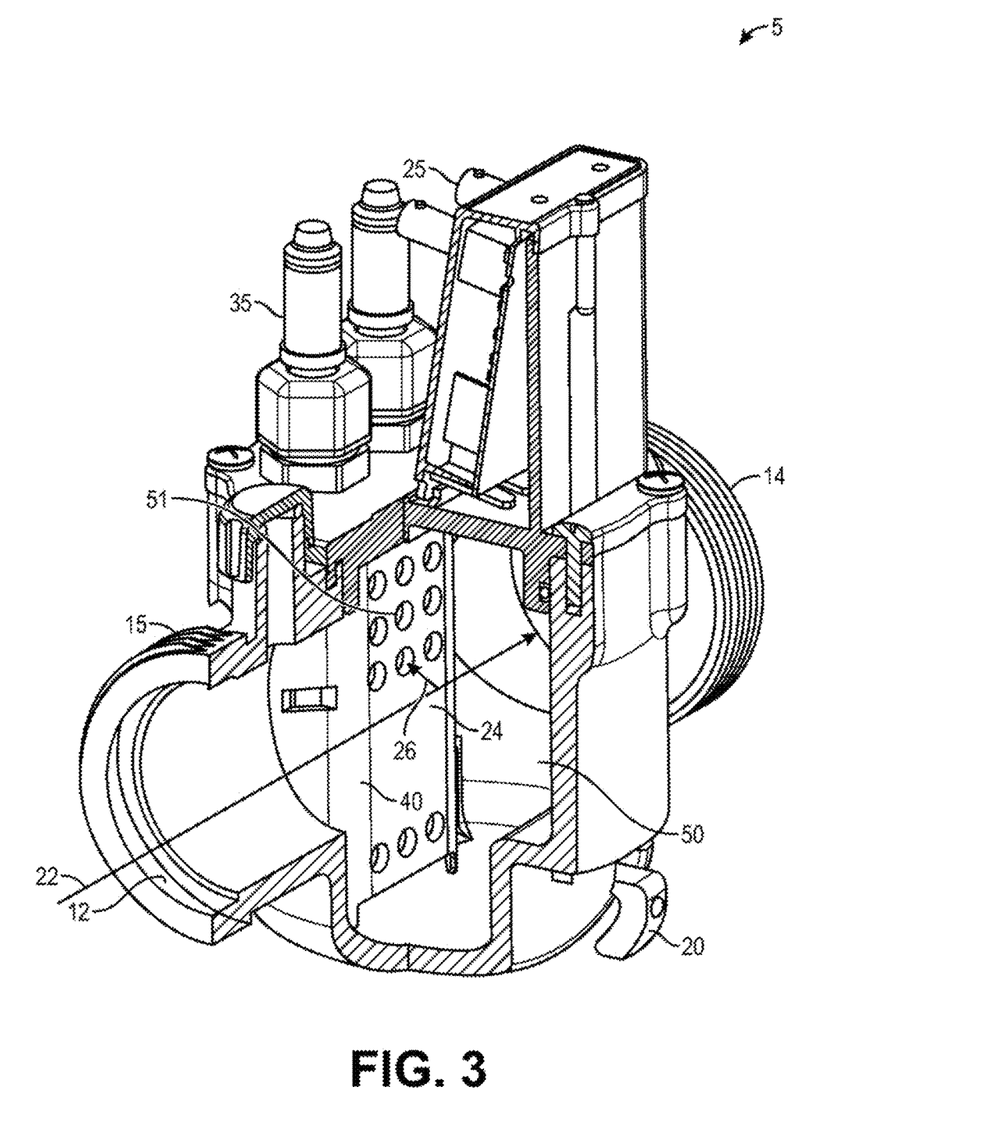
FIG. 3 is a partial-section view of the plumbed in-line sensor system of FIG. 1.
Figure 4A:
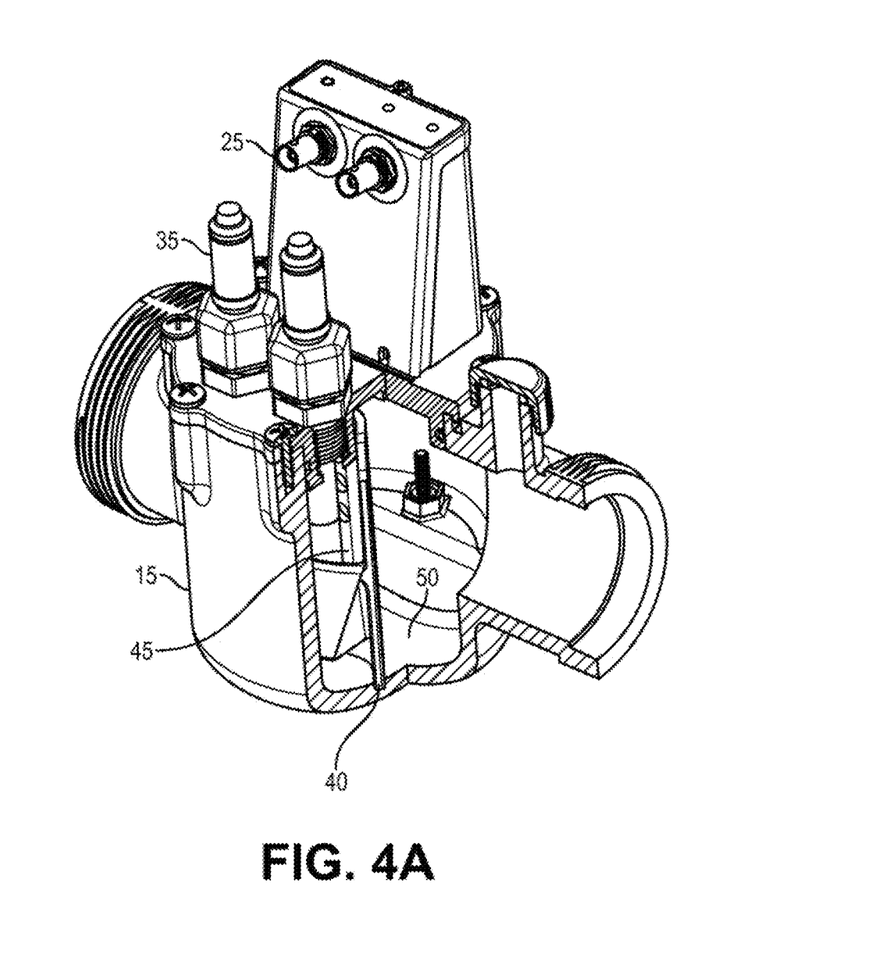
FIG. 4A is another partial-section view of the plumbed in-line sensor system of FIG. 1.
Figure 4B:
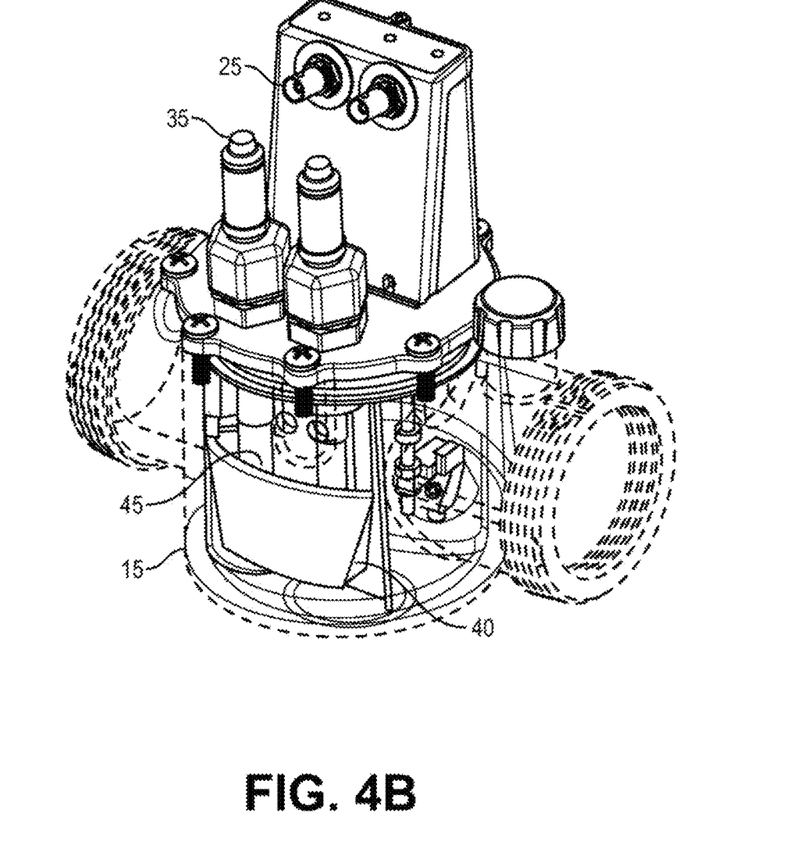
FIG. 4B is a partially-transparent view of the plumbed in-line sensor system of FIG. 1.

FIGS. 3 and 4A-4B illustrate an exemplary assembled view of a plumbed in-line sensor system. The sensor system is installed with the pipe 15 and includes the water bond 20 (FIG. 3), the sensor ports 25, and the sensors 35 as previously described. The plumbed in-line sensor system additionally includes the sensor housing 40. As noted above and as illustrated in FIG. 3, the sensor housing 40 is positioned within the cavity 50 of the pipe 15 and within a path of water flowing between the inlet 12 and the outlet 14 (represented by arrow 22) of the pipe 15. The sensor housing 40 is configured to limit the amount of water from the main flow 22 that can reach the sensors 35 surrounded by the sensor housing 40. In this way, the sensors 35 are not subjected to the main flow 22 of water flowing between the inlet 12 and the outlet 14, even though the sensor housing 40 itself is positioned within the path of the main flow 22.

The sensor housing 40 may include a baffle 24 and a well 45 (FIGS. 4A-4B). The baffle 24 is configured to divert a portion of the water flowing between the inlet 12 and the outlet 14 (represented by arrow 22) to an area around the sensors 35 (as indicated by arrow 26). The baffle 24 may include one or more openings 51 for water to flow through to reach the area around the sensors 35. In some cases, the baffle 24 directs the water through the openings into an interior of the sensor housing 40 and to an area around the sensors 35, where the area around the sensors is shielded from the path of the main flow 22 of water. Diverting a portion of the main water flow in this way can increase the life of the sensors 35. In some cases, the baffle 24 is also designed to slow the water that is diverted to the one or more sensors 35.

Figure 5:
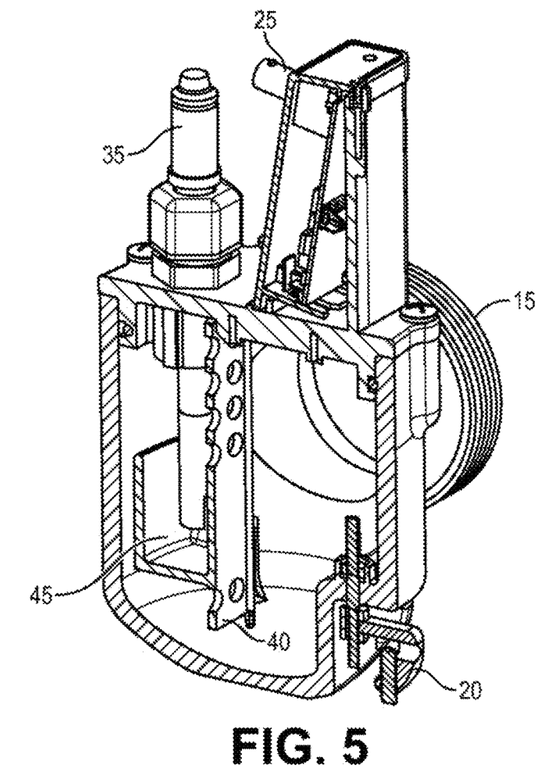
FIG. 5 is a section view of the plumbed in-line sensor system of FIG. 1.

FIG. 5 illustrates an exemplary section view of the plumbed in-line sensor system. The sensor housing 40 includes a well 45 for collecting and retaining water at the one or more sensors 35 (e.g., for retaining water that has been diverted into the sensor housing at least at a tip of the sensors 35). The well 45 may ensure water remains around the sensors 35 even if the pipe 15 is drained or if water is otherwise no longer flowing through the pipe 15 between the inlet 12 and the outlet 14, so that the sensors 35 are not damaged.

Figure 6A:
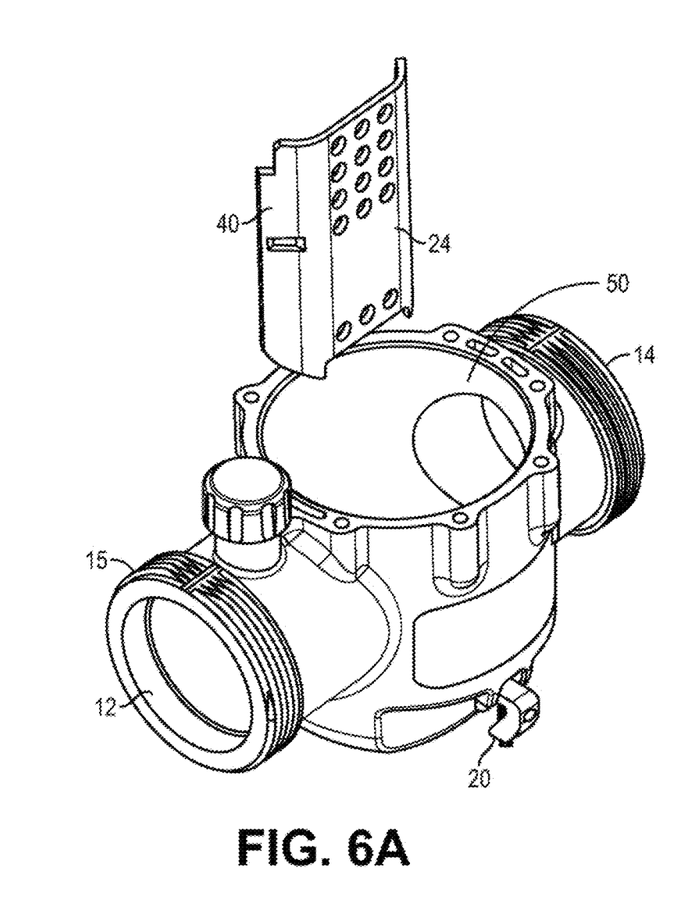
FIGS. 6A-6C illustrate exemplary views of the sensor housing of the plumbed in-line sensor system of FIG. 1.
Figure 6B:
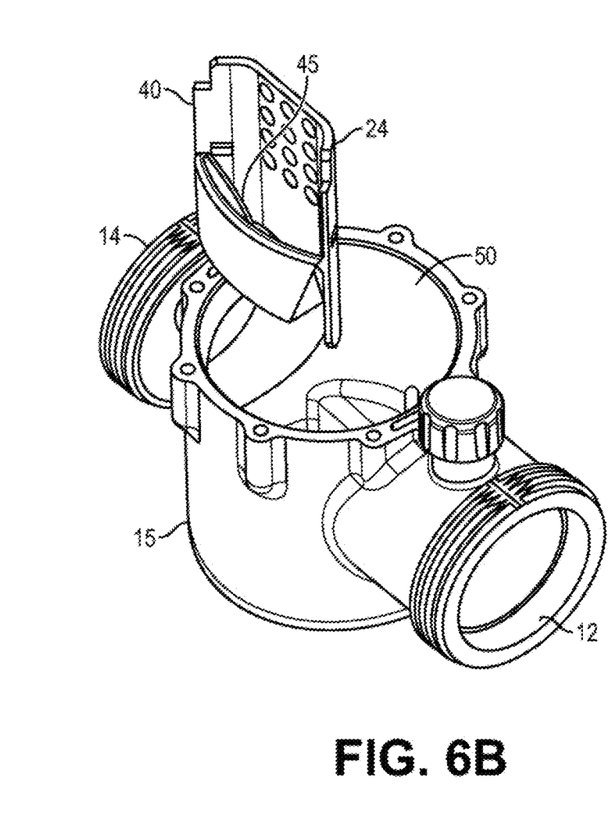
Figure 6C:
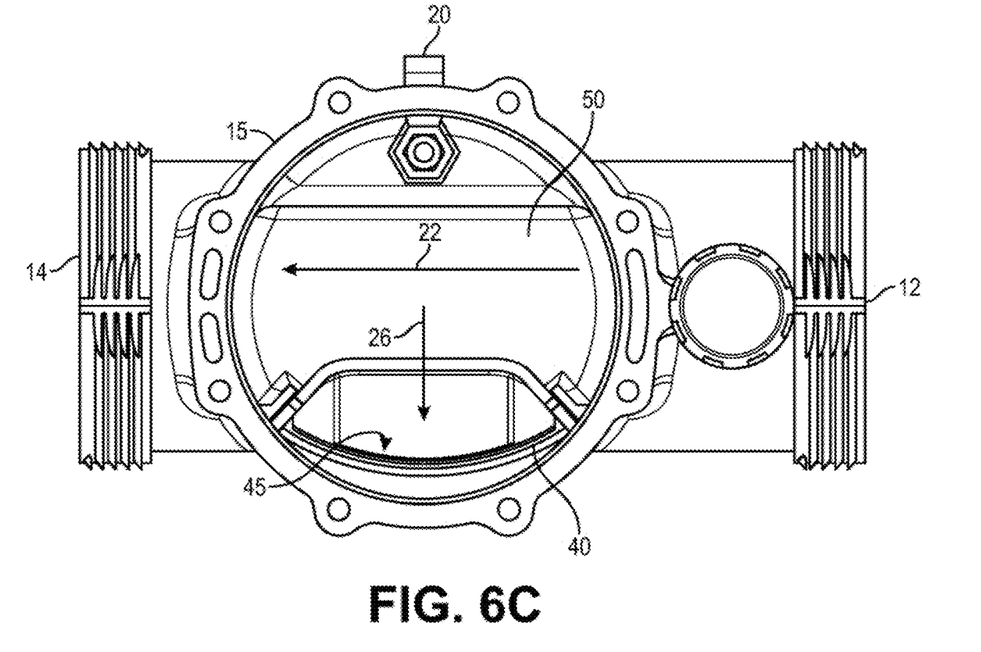

FIGS. 6A-6C illustrate exemplary views of the sensor housing 40 of the plumbed in-line sensor system. As noted above, the sensor housing 40 may be positioned within the cavity 50 of the pipe 15 between the inlet 12 and the outlet 14 so that water flowing between the inlet 12 and the outlet 14 encounters the baffle 24 of the sensor housing 40. Once the water flow encounters the baffle 24, a portion of the main water flow 22 is diverted into the well 45 of the sensor housing 40 (as indicated by arrow 26 in FIG. 6C) and into contact with the one or more sensors 35, such as via the openings in the baffle 24. Otherwise, the sensor housing 40 prevents the non-diverted main flow of water from reaching the interior of the sensor housing and thus from reaching an area containing the sensors 35. In one non-limiting embodiment, the diverted water flow 26 is perpendicular or generally perpendicular to the main water flow 22, although it need not be.

A collection of exemplary embodiments are provided below, including at least some explicitly enumerated as "Illustrations" providing additional description of a variety of example embodiments in accordance with the concepts described herein. These illustrations are not meant to be mutually exclusive, exhaustive, or restrictive; and the disclosure not limited to these example illustrations but rather encompasses all possible modifications and variations within the scope of the issued claims and their equivalents.

Illustration A. A sensor system for determining properties of swimming pool or spa water, wherein the sensor system comprises one or more sensors, and wherein the one or more sensors are positioned in a sensor housing located within a cavity of a pipe and in-line with an inlet and an outlet of the pipe, wherein the sensor housing is configured to divert a portion of water flowing through the cavity to an interior of the sensor housing and to an area around the sensors, and to maintain at least some of the diverted water in the area around the sensors even if the water is not flowing through or is drained from the pipe.

Illustration B. The sensor system of any preceding or subsequent illustrations or combination of illustrations, wherein the sensor housing comprises a baffle configured to divert the portion of water to the area around the sensors.

Illustration C. The sensor system of any preceding or subsequent illustrations or combination of illustrations, further comprising a water bond coupled to the pipe configured to protect the sensors from stray current.

Illustration D. The sensor system of any preceding or subsequent illustrations or combination of illustrations, wherein the diverted water flows perpendicular to the water flowing between the cavity from the inlet to the outlet of the pipe.

Illustration E. The sensor system of any preceding or subsequent illustrations or combination of illustrations, wherein the sensors are configured to measure an oxidative reduction potential and/or a pH of the water.

Illustration F. The sensor system of any preceding or subsequent illustrations or combination of illustrations, further comprising an electronic assembly configured to receive measurements from the sensors.

Illustration G. The sensor system of any preceding or subsequent illustrations or combination of illustrations, further comprising a cover coupled to the sensor housing and positioned over the sensors and the electronic assembly.

Illustration H. A sensor system, comprising: a sensor; and a sensor housing within a cavity of a pipe configured to: limit an amount of water flowing through the cavity that reaches the sensor; slow a speed of the limited amount of water before it reaches the sensor; and/or maintain a presence of at least some of the limited amount of water in contact with the sensor, even if the pipe is drained or water no is flowing through the cavity.

Illustration I. The sensor system of any preceding or subsequent illustrations or combination of illustrations, wherein the sensor housing is configured to: limit the amount of water flowing through the cavity that reaches the sensor; and maintain the presence of at least some of the limited amount of water in contact with the sensor, even if the pipe is drained or water no is flowing through the cavity.

Illustration J. The sensor system of any preceding or subsequent illustrations or combination of illustrations, wherein the sensor housing is configured to: limit the amount of water flowing through the cavity that reaches the sensor; slow the speed of the limited amount of water before it reaches the sensor; and maintain the presence of at least some of the limited amount of water in contact with the sensor, even if the pipe is drained or water no is flowing through the cavity.

Illustration K. The sensor system of any preceding or subsequent illustrations or combination of illustrations, wherein the sensor housing is configured to: slow the speed of the limited amount of water before it reaches the sensor; and maintain the presence of at least some of the limited amount of water in contact with the sensor, even if the pipe is drained or water no is flowing through the cavity.

Illustration L. The sensor system of any preceding or subsequent illustrations or combination of illustrations, wherein the sensor housing is configured to: limit the amount of water flowing through the cavity that reaches the sensor; and slow the speed of the limited amount of water before it reaches the sensor.

Illustration M. The sensor system of any preceding or subsequent illustrations or combination of illustrations, wherein the sensor housing is in-line with an inlet and an outlet of the pipe, wherein the sensor housing is configured to divert a portion of water flowing through the cavity to an interior of the sensor housing that reaches the sensor.

Illustration N. The sensor system of any preceding or subsequent illustrations or combination of illustrations, wherein the sensor housing comprises a baffle including one or more openings configured to limit the amount of water flowing through the cavity that reaches the sensor and slow the speed of the limited amount of water before it reaches the sensor.

Illustration O. The sensor system of any preceding or subsequent illustrations or combination of illustrations, wherein the sensor housing comprises a well configured to maintain the presence of at least some of the limited amount of water in contact with the sensor.

Illustration P. The sensor system of any preceding or subsequent illustrations or combination of illustrations, wherein the sensor is configured to measure an oxidative reduction potential and/or a pH of the water.

Illustration Q. The sensor system of any preceding or subsequent illustrations or combination of illustrations, further comprising an electronic assembly configured to receive measurements from the sensor.

Illustration R. The sensor system of any preceding or subsequent illustrations or combination of illustrations, further comprising a computing system configured to determine, based on sensor data received from the sensor, whether one or more properties of the water are outside a predefined threshold.

Illustration S. A sensor system, comprising: a sensor; and a sensor housing within a cavity of a pipe, wherein the sensor housing houses at least a portion of the sensor and controls how much water moving through the cavity of the pipe reaches the sensor, wherein the sensor system is configured to: determine, based on sensor data from the sensor, if (i) an oxidative reduction potential of the water is below a predefined threshold and/or (ii) a pH of the water is outside a predefined range; and output an indicator based on the determination.

Illustration T. The sensor system of any preceding or subsequent illustrations or combination of illustrations, wherein the sensor housing comprises a baffle including one or more openings configured to control how much water moving through the cavity reaches the sensor.

Illustration U. The sensor system of any preceding or subsequent illustrations or combination of illustrations, wherein the baffle is further configured to slow a speed of the water before it reaches the sensor.

Illustration V. The sensor system of any preceding or subsequent illustrations or combination of illustrations, wherein the sensor housing comprises a well configured to maintain at least some of the water that reaches the sensor in an area around the sensor even if the water is not flowing through or is drained from the pipe.

Illustration W. The sensor system of any preceding or subsequent illustrations or combination of illustrations, further comprising an electronic assembly configured to receive the sensor data from the sensor.

Illustration X. The sensor system of any preceding or subsequent illustrations or combination of illustrations, further comprising a water bond configured to protect the sensor from stray current.

Illustration Y. A sensor system for determining properties of swimming pool or spa water, the sensor system comprising a sensor and a sensor housing within a cavity of a pipe, wherein the sensor housing houses at least a portion of the sensor, controls how much water moving through the cavity of the pipe reaches the sensor, and comprises a well configured to maintain the presence of at least some of the water in contact with the sensor.

Illustration Z. A sensor system for determining properties of swimming pool or spa water, comprising a sensor and a sensor housing within a cavity of a pipe, wherein the sensor housing houses at least a portion of the sensor and controls how much water moving through the cavity of the pipe reaches the sensor and wherein the sensor housing comprises an integrated water bond configured to protect the sensor from stray current.

Illustration AA. A sensor system for determining properties of swimming pool or spa water, comprising a sensor, a sensor housing within a cavity of a pipe, wherein the sensor housing houses at least a portion of the sensor and controls how much water moving through the cavity of the pipe reaches the sensor, and an electronic assembly for receiving sensor data from the sensor, wherein the electronic assembly is integrated with the sensor housing.

Although applicant has described devices and techniques for use principally with swimming pools and spas, persons skilled in the relevant field will recognize that the present invention may be employed in connection with other objects and in other manners. Finally, references to "pools" and "swimming pools" herein may also refer to spas or other water containing vessels used for recreation or therapy and for which cleaning is needed or desired.

The foregoing is provided for purposes of illustrating, explaining, and describing embodiments of the present invention. Modifications and adaptations to these embodiments, including combinations of various features, will be apparent to those skilled in the art and may be made without departing from the scope or spirit of the invention. For avoidance of doubt, any combination of features not physically impossible or expressly identified as non-combinable herein may be within the scope of the invention.

The invention claimed is:

1. A sensor system for determining properties of swimming pool or spa water, wherein the sensor system comprises one or more sensors, and wherein the one or more sensors are positioned in a sensor housing located within a cavity of a pipe and in-line with an inlet and an outlet of the pipe, wherein the sensor housing is configured to divert a portion of water flowing through the cavity to an interior of the sensor housing and to an area around the one or more sensors, and to maintain at least some of the diverted water in the area around the one or more sensors even if the water is not flowing through or is drained from the pipe, the area around the one or more sensors between the sensor housing and a wall of the pipe defining the cavity.

2. The sensor system of claim 1, wherein the sensor housing comprises a baffle configured to divert the portion of water to the area around the one or more sensors.

3. The sensor system of claim 1, further comprising a water bond coupled to the pipe configured to protect the one or more sensors from stray current.

4. The sensor system of claim 1, wherein the diverted water flows perpendicular to the water flowing between the cavity from the inlet to the outlet of the pipe.

5. The sensor system of claim 1, wherein the one or more sensors are configured to measure an oxidative reduction potential and/or a pH of the water.

6. The sensor system of claim 1, further comprising an electronic assembly configured to receive measurements from the one or more sensors.

7. The sensor system of claim 6, further comprising a cover coupled to the sensor housing and positioned over the one or more sensors and the electronic assembly.

8. A sensor system for a pipe, comprising:
a sensor; and
a sensor housing within a cavity of the pipe, the sensor housing comprising a baffle comprising a first side and a second side, wherein the first side configured to face a main flow of water flowing through the cavity, and wherein at least a portion of the sensor is between the second side and a wall of the pipe defining the cavity, wherein the sensor housing is configured to:

limit an amount of water flowing through the cavity that reaches the sensor;

slow a speed of the limited amount of water before it reaches the sensor; and/or maintain a presence of at least some of the limited amount of water in contact with the sensor, even if the pipe is drained or water no is flowing through the cavity.

9. The sensor system of claim 8, wherein the sensor housing is configured to:

limit the amount of water flowing through the cavity that reaches the sensor; and maintain the presence of at least some of the limited amount of water in contact with the sensor, even if the pipe is drained or water no is flowing through the cavity.

10. The sensor system of claim 8, wherein the sensor housing is configured to:

limit the amount of water flowing through the cavity that reaches the sensor;

slow the speed of the limited amount of water before it reaches the sensor; and maintain the presence of at least some of the limited amount of water in contact with the sensor, even if the pipe is drained or water no is flowing through the cavity.

11. The sensor system of claim 8, wherein the sensor housing is configured to:

slow the speed of the limited amount of water before it reaches the sensor; and maintain the presence of at least some of the limited amount of water in contact with the sensor, even if the pipe is drained or water no is flowing through the cavity.

12. The sensor system of claim 8, wherein the sensor housing is configured to:

limit the amount of water flowing through the cavity that reaches the sensor; and slow the speed of the limited amount of water before it reaches the sensor.

13. The sensor system of claim 8, wherein the sensor housing is in-line with an inlet and an outlet of the pipe, wherein the sensor housing is configured to divert a portion of water flowing through the cavity to an interior of the sensor housing that reaches the sensor.

14. The sensor system of claim 8, wherein the baffle comprises one or more openings configured to limit the amount of water flowing through the cavity that reaches the sensor and slow the speed of the limited amount of water before it reaches the sensor.

15. The sensor system of claim 8, wherein the sensor housing comprises a well configured to maintain the presence of at least some of the limited amount of water in contact with the sensor.

16. The sensor system of claim 8, wherein the sensor is configured to measure an oxidative reduction potential and/or a pH of the water.

17. The sensor system of claim 8, further comprising an electronic assembly configured to receive measurements from the sensor.

18. The sensor system of claim 8, further comprising a computing system configured to determine, based on sensor data received from the sensor, whether one or more properties of the water are outside a predefined threshold.

19. A sensor system, comprising:

a sensor; and a sensor housing within a cavity of a pipe, wherein the sensor housing is configured to house at least a portion of the sensor within the cavity and between the sensor housing and a wall of the pipe defining the cavity, and wherein the sensor housing controls how much water moving through the cavity of the pipe reaches the sensor, wherein the sensor system is configured to:

determine, based on sensor data from the sensor, if (i) an oxidative reduction potential of the water is below a predefined threshold and/or (ii) a pH of the water is outside a predefined range; and output an indicator based on the determination.

20. The sensor system of claim 19, wherein the sensor housing comprises a baffle including one or more openings configured to control how much water moving through the cavity reaches the sensor.

21. The sensor system of claim 20, wherein the baffle is further configured to slow a speed of the water before it reaches the sensor.

22. The sensor system of claim 19, wherein the sensor housing comprises a well configured to maintain at least some of the water that reaches the sensor in an area around the sensor even if the water is not flowing through or is drained from the pipe.

23. The sensor system of claim 19, further comprising an electronic assembly configured to receive the sensor data from the sensor.

24. The sensor system of claim 19, further comprising a water bond configured to protect the sensor from stray current.

25. A sensor system for determining properties of swimming pool or spa water, the sensor system comprising:

a sensor; and a sensor housing within a cavity of a pipe, wherein the sensor housing:

houses at least a portion of the sensor; and comprises (i) a baffle comprising a first side and a second side and (ii) a well on the second side of the baffle and between a wall of the pipe and the baffle, the well configured to maintain the presence of at least some of the water in contact with the sensor.

26. A sensor system for determining properties of swimming pool or spa water, the sensor system comprising:

a sensor;

a sensor housing within a cavity of a pipe, wherein the sensor housing houses at least a portion of the sensor within the cavity and between the sensor housing and a wall of the pipe defining the cavity and controls how much water moving through the cavity of the pipe reaches the sensor; and an electronic assembly for receiving sensor data from the sensor, wherein the electronic assembly is integrated with the sensor housing.

* * * * *